US008536883B2

(12) United States Patent  (10) Patent No.: US 8,536,883 B2
Xie et al.  (45) Date of Patent: Sep. 17, 2013

(54) METHOD OF MEASURING A MULTIPHASE FLOW

(75) Inventors: Cheng-gang Xie, Sawston (GB); Mehdi Hizem, Paris (FR); Rolf Rustad, Raadal (NO)

(73) Assignee: Schlumberger Technology Corporation, Sugar Land, TX (US)

( * ) Notice: Subject to any disclaimer, the term of this patent is extended or adjusted under 35 U.S.C. 154(b) by 405 days.

(21) Appl. No.: 12/769,781

(22) Filed: Apr. 29, 2010

(65) Prior Publication Data

US 2011/0267074 A1 Nov. 3, 2011

(51) Int. Cl.
| G01R 27/08 | (2006.01) |
| G01V 3/18 | (2006.01) |
| G01V 3/00 | (2006.01) |
| G01F 1/68 | (2006.01) |
| G01N 33/20 | (2006.01) |
| G01N 37/00 | (2006.01) |
| H01Q 13/00 | (2006.01) |

(52) U.S. Cl.
USPC ........ 324/691; 324/324; 324/338; 73/204.11; 73/61.44; 73/61.43; 343/772

(58) Field of Classification Search
USPC .................................. 324/691, 637; 73/61.44
See application file for complete search history.

(56) References Cited

U.S. PATENT DOCUMENTS

| 3,849,721 A | 11/1974 | Calvert |
| 3,891,391 A * | 6/1975 | Boone .................. 73/204.18 |
| 3,944,910 A | 3/1976 | Rau |
| 4,704,581 A | 11/1987 | Clark |
| 5,243,290 A | 9/1993 | Safinya et al. |
| 5,453,693 A * | 9/1995 | Sinclair et al. ................ 324/324 |
| 5,485,743 A * | 1/1996 | Taherian et al. ............. 73/61.44 |
| 5,793,216 A | 8/1998 | Constant |
| 6,097,786 A * | 8/2000 | Groves et al. .................... 378/53 |
| 6,658,944 B2 * | 12/2003 | Melnikov et al. .......... 73/861.04 |

(Continued)

FOREIGN PATENT DOCUMENTS

| EP | 1901094 | 3/2008 |
| EP | 1983357 | 10/2008 |

(Continued)

OTHER PUBLICATIONS

International Search Report and Written Opinion of PCT Application No. PCT/IB2011/000514 dated Dec. 26, 2011.

Primary Examiner — Jermele M Hollington
Assistant Examiner — Christopher McAndrew

(57) ABSTRACT

A method of measuring the permittivity and/or conductivity of a multiphase fluid flowing through a conduit is provided. The method includes the steps of measuring the signal from a first electromagnetic transmitter to a first electromagnetic receiver separated by a first distance, measuring the signal from the first electromagnetic transmitter to a second electromagnetic receiver separated by a second distance, measuring the signal from a second electromagnetic transmitter to the first electromagnetic receiver separated by a distance substantially equal to the second distance, measuring the signal from the second electromagnetic transmitter to the second electromagnetic receiver separated by a distance substantially equal to the first distance, and wherein the first and second distances are substantially different. This is followed by the step of combining the four signals to obtain a measurement of the phase-shift and amplitude-attenuation substantially independent of the gain values applied to the receivers and transmitters to provide an estimate of the mixture permittivity and/or conductivity of the multiphase fluid.

10 Claims, 5 Drawing Sheets

(56) References Cited

U.S. PATENT DOCUMENTS

| | | |
|---|---|---|
| 6,831,470 B2 | 12/2004 | Xie et al. |
| 6,940,286 B2 * | 9/2005 | Wang et al. .................. 324/450 |
| 7,363,160 B2 | 4/2008 | Seleznev et al. |
| 7,376,514 B2 | 5/2008 | Habashy et al. |
| 7,469,188 B2 * | 12/2008 | Wee ................................ 702/45 |
| 7,481,118 B2 * | 1/2009 | Nyfors ............................ 73/861 |
| 7,503,227 B2 * | 3/2009 | Davis et al. ................ 73/861.42 |
| 7,624,652 B2 | 12/2009 | Wee et al. |
| 2008/0224705 A1 | 9/2008 | Simon et al. |
| 2009/0126502 A1 * | 5/2009 | Wee et al. .................. 73/861.04 |

FOREIGN PATENT DOCUMENTS

| | | |
|---|---|---|
| EP | 2015109 A1 | 1/2009 |
| GB | 2430493 | 3/2007 |
| WO | 2007129897 A1 | 11/2007 |
| WO | 2009010132 A2 | 1/2009 |

\* cited by examiner

METHOD OF MEASURING A MULTIPHASE FLOW

TECHNICAL FIELD

The invention relates to a method of measuring a multiphase flow comprising a mixture of a gas phase, an oil phase and a water phase.

BACKGROUND

It is desirable during the production of oil and gas to carry out flow measurements to determine the flow rates of individual phases of multiphase flow. In particular, measurement of the volume fractions and flow velocities of e.g. oil, gas and water in a conduit, such as a pipe, is highly desirable.

However, in general it is very difficult to obtain measurements of the flow of the different phases when they flow simultaneously through a pipe.

This difficulty is primarily due to the wide variety of flow regimes such a multiphase flow can take. For example, the three phases can be well mixed together with one as the continuous phase and the other two dispersed within it. Mostly there is phase separation between gas and liquid with the liquid often moving at a much lower velocity than the gas.

When gas is the dominant phase, a commonly encountered flow regime in a vertical pipe is for the gas to travel along the centre of the pipe with dispersed droplets of oil and water within it, whilst the majority of the oil and water travels along the pipe wall which itself may comprise entrained gas bubbles.

Additionally, flow phase and velocity distributions may alter both spatially and temporally. Sudden or gradual variation in flow rates of one phase or another may cause a change in flow regime. Also, due to the high pressure encountered deep underground, a flow which is mixed or in bubble-flow can become dominated by a discernible high gas fraction as the pressure drops nearer the surface and the gas expands and/or comes out of solution.

Multiphase flowmeters are available and have been suggested in the prior art.

The use of electromagnetic methods, such as microwaves, has been suggested because of their high measurement sensitivity to the presence of the water phase in a multiphase flow (water permittivity/conductivity is much higher than the permittivity/conductivity of the hydrocarbon oil-gas phases). U.S. Pat. No. 6,831,470 of the Applicant teaches the use of a microwave open-ended coaxial reflection probe to measure the mixture permittivity and mixture conductivity to obtain an online estimate of water conductivity of a multiphase flow. An estimate of the water-to-liquid ratio (WLR) immune to water-salinity change is also possible if the liquid layer in the vicinity of the probe is substantially free of entrained gas and has a thickness higher than the probe's depth of investigation.

U.S. Pat. No. 7,908,930 of the Applicant utilises a transmission electromagnetic approach, in combination with a venturi differential-pressure sensor (for total flow rate) and a gamma-ray radiation sensor (for gas-liquid mixture density). The across-pipe transmission microwaves are used to measure the mixture permittivity and mixture conductivity over the vertical pipe cross-section of the venturi throat, for water and hydrocarbon (oil/gas) discrimination. The gamma rays are employed in the same venturi-throat pipe cross-section for gas and liquid (oil/water) discrimination, by measuring the average fluid mixture density across pipe. By employing three-phase density and permittivity and/or conductivity mixing rules, measures of water fraction, oil fraction (hence of the WLR) and gas fraction can be obtained. Measured venturi differential pressure and/or further microwave sensors in the venturi for flow velocity can be used to provide an estimate of the individual phase flow rate, from the measured individual phase fraction and the total flow rate and/or the phase velocity data. As disclosed in U.S. Pat. No. 6,831,470, RF/microwave transmission approach also permits online water-conductivity estimate from the measured mixture permittivity and mixture conductivity.

U.S. Pat. No. 5,485,743 of the Applicant discloses a method for measuring multiphase flows in a pipe using an array (e.g. twelve) of microwave antennas arranged around the pipe. Each antenna is capable of transmitting microwave energy (at one or more frequencies) into the pipe and detecting propagated microwave energy in the pipe. Microwave energy from each antenna is transmitted in turn while the propagated microwave energy is detected at the non-transmitting antennas so as to generate multiple amplitude-attenuation and phase-shift output signals. The output signals from all antennas combinations are interpreted by an appropriate mathematical inversion algorithm, e.g. as flow permittivity-conductivity cross-sectional/tomographic images, so as to measure the flow phase fractions and to visualise flow phase distributions in the pipe. Only absolute measurements are disclosed and no differential-measurement scheme (of measuring amplitude-attenuation ratio and phase-shift difference of chosen two receivers, with respect to one chosen transmitter) is mentioned.

U.S. Pat. No. 7,624,652 discloses a differential-measurement configuration based on one transmitter and two receivers, where the amplitude-attenuation ratio and/or phase-shift difference of the two receivers, measured at multiple frequencies with respect to a chosen transmitter, are used for flow-mixture dielectric-constant determination.

In all of these electromagnetic methods, a measure of the permittivity and conductivity of the flow mixture is involved by analysing phase-shift and amplitude-attenuation. Permittivity and/or conductivity data allows a host of useful flow information within the conduit to be obtained, such as water conductivity, water fraction, WLR, flow rates of individual phases, in combination with a differential pressure and a nuclear mixture-density measurement; information as to the distribution of fluid phases within the conduit can be obtained from measurements of a plurality of RF/microwave antennas arranged around the conduit.

SUMMARY OF THE INVENTION

In all of the prior art methods, the estimate of the permittivity and/or conductivity involves taking into account factors influencing the quality of the transmitted and/or received signal, such as the thermal stability of the electronics-circuit amplification-gain applied to the receiving and/or transmitting antennas, the variations in the antennas' connecting cables and/or in the antennas' load impedances due to e.g. changes in fluid temperature or aging etc.

This is normally not a problem in a controlled laboratory environment, since such factors are usually known and can be accounted for by appropriate calibrations and/or corrections. However, in a permanent or unmanned oilfield measurement environment such as offshore and/or subsea, gain levels in the electronics measurement circuits can drift over time and/or with temperature. Additionally, the transmitted and/or received signal may be affected by other factors, such as a build-up of wax material in front of the antenna, aging of the circuitry etc. These latter problems can be particularly problematic when the flow measurement is taken in an oilfield environment, where very high pressures and temperatures exacerbate these factors.

An improved method of measuring phase-shift and amplitude-attenuation that is immune to these influencing factors would be highly desirable.

Thus, the invention relates to a method of measuring the permittivity and/or conductivity of a multiphase fluid flowing through a conduit, the method comprising the steps of measuring the signal from a first electromagnetic transmitter to a first electromagnetic receiver separated by a first distance, measuring the signal from the first electromagnetic transmitter to a second electromagnetic receiver separated by a second distance, measuring the signal from a second electromagnetic transmitter to the first electromagnetic receiver separated by a distance substantially equal to the second distance, measuring the signal from the second electromagnetic transmitter to the second electromagnetic receiver separated by a distance substantially equal to the first distance, and wherein the first and second distances are substantially different, followed by combining the four signals to obtain a measurement of the phase-shift and amplitude-attenuation substantially independent of the gain values applied to the receivers and transmitters to provide an estimate of the mixture permittivity and/or conductivity of the multiphase fluid.

Thus, by combining the four signals in a particular manner it has been found to be possible to obtain a measure of phase-shift and amplitude-attenuation which is substantially independent of factors other than those provided by the multiphase fluid travelling through the conduit. Therefore, a more accurate estimate of permittivity and/or conductivity can be obtained and the accuracy is maintained over time, despite drifts which may occur in the gain values of the measurement paths related to both the transmitting and the receiving antennas.

The value of permittivity obtained is also called complex permittivity. From this value, the "true" permittivity characterizing energy storage and the conductivity due to energy-dissipation losses can be obtained in a known manner, given the measurement frequency.

Typically, the transmitting and receiving antennas are able to operate as a pure magnetic dipole and/or as a pure electric dipole. Preferably they are capable of operating as both pure magnetic and pure electric dipoles.

For example, a simple antenna would be an open-ended coaxial probe that behaves as electric dipoles. A more elaborate design of antenna is shown in EP 1901 094 of the Applicant which is a cross-dipole of pure magnetic-dipole antennas. The orthogonality of the two cross dipole modes is ensured with a high degree of isolation. Antenna as a superposition of a substantially pure electric dipole and a substantially pure magnetic dipole is shown in EP 1983 357 of the Applicant.

The signals are transmitted and received at one or more frequencies in the radio frequency (RF) and/or microwave frequency spectrum. Thus, the signals typically have a frequency or multiple frequencies of from 10 MHz to 10 GHz.

The method of the invention relies on using at least two transmitters and at least two receivers for each measurement frequency. The four available signals are then combined to eliminate undesirable influencing factors. An essential element of the invention is that the distance between a first transmitter and a first receiver (the first distance) and that between the first transmitter and a second receiver (the second distance) are significantly different to each other. This means that the difference of the first and the second distance is at least 10%, more preferably at least 20%.

Another essential element of the invention is that the distance between a second transmitter and the first receiver is substantially equal to the second distance. Also the distance between a second transmitter to the second receiver is substantially equal to the first distance. As used herein, the term "substantially equal" means that the distances are within 1% of the first and second distance respectively, preferably within 0.5%.

Typically the conduit has a circular cross-section (but not limited to a circular cross-section). The transmitters and receivers are typically flush-mounted on the inside face of the conduit. The transmitters and receivers may be located at the same axial plane of the conduit or they may be positioned at differing axial planes.

In a second aspect, the invention relates to a multiphase flowmeter comprising at least two electromagnetic transmitters and at least two electromagnetic receivers, coupled with electromagnetic generation and reception circuitry respectively, and coupled to a microprocessor, wherein the transmitters, receivers, circuitry and the microprocessor are arranged to carry out the method described herein.

When the conduit has a circular cross-section and the transmitters and receivers are all arranged in the same axial position, the spacing requirements of the invention requires that they be arranged substantially with a line of symmetry passing through the centre of the conduit. This means that the second transmitter and second receiver must be positioned in effective mirror image positions relative to the first transmitter and first receiver respectively about the centre line of symmetry. This ensures that the relative positioning and spacing requirements of the invention are met.

It is possible to involve more than two transmitters and/or more than two receivers. Additional transmitters and receivers can give further improvements in accuracy and/or in versatility by covering different regions or depths of a pipe cross section and/or of different pipe cross sections, however only the basic combinations of two of each at a time are necessary in order to eliminate the undesirable factors affecting the signals. Therefore, there is a tomography flow imaging capability from having additional transmitters and receivers in the same cross-sectional plane and/or in different cross-sectional planes. However, a modest number of antennas acting as transmitters or receivers or both, say up to sixteen in a cross-sectional plane, can be advantageously chosen as a full tomography system. Additionally, for a non-tomography system, from two to six transmitters provides a good balance between measurement speed, pipe-area coverage, accuracy and cost.

The method of the invention involves an operation carried out on four "absolute" measurements. Thus, an arrangement with more than two transmitters or more than two receivers will generate more than one set of four "absolute measurements". For example, an arrangement with two transmitters and four receivers can generate eight absolute measurements. From these eight measurements it is possible to generate two separate groups (each group being related to each transmitter) of four absolute readings. Thus, two compensated (transmitter-receiver path gain-immune) measurements according to the invention can be generated by differencing the same group and averaging the group-differences appropriately to provide greater accuracy.

Another advantage of having more than two transmitters or more than two receivers is that they can be arranged around the conduit to probe different regions or depths of the conduit.

For example two transmitters could be positioned, say 30° apart. Two receivers could then be positioned each a further 30° from the transmitters. Two additional receivers could then be positioned opposite the respective transmitters. By use of the "near" receivers, information on the condition in the vicinity of the inner wall of the conduit can be obtained. By use of the "far" receivers, information on the cross-pipe diameter can be obtained. Such measurements may be combined to derive further information on the spatial distribution of the phases of the flow. Thus, the first distance may span substantially across the conduit and the second distance may span substantially adjacent an inside wall of the conduit.

The water fraction of the multiphase flow mixture (e.g. the water-in-liquid ratio of the liquid annulus in the case of an annular flow) and the gas fraction of the flow mixture (e.g. the gas-core diameter in the case of annular flow) can be derived from the mixture permittivity and conductivity of the flow by the use of appropriate permittivity and conductivity mixing rules. The water conductivity (salinity) can also be determined from the mixture permittivity and conductivity (see U.S. Pat. No. 6,831,470), so that water fraction and WLR estimates can take account of any changes in salinity.

The invention will now be illustrated by reference to the following Figures, in which.

Figure 1A:
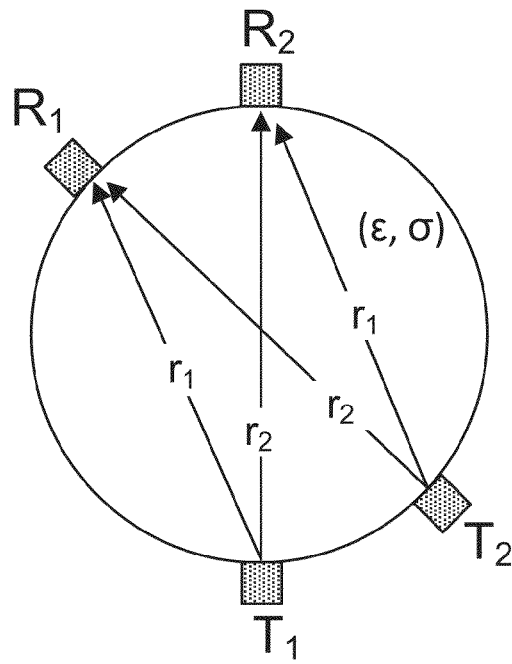
FIG. 1A is a schematic representation of a cross-sectional view through a conduit comprising two transmitters and two receivers arranged to carry out the method of the present invention.
Figure 1B:
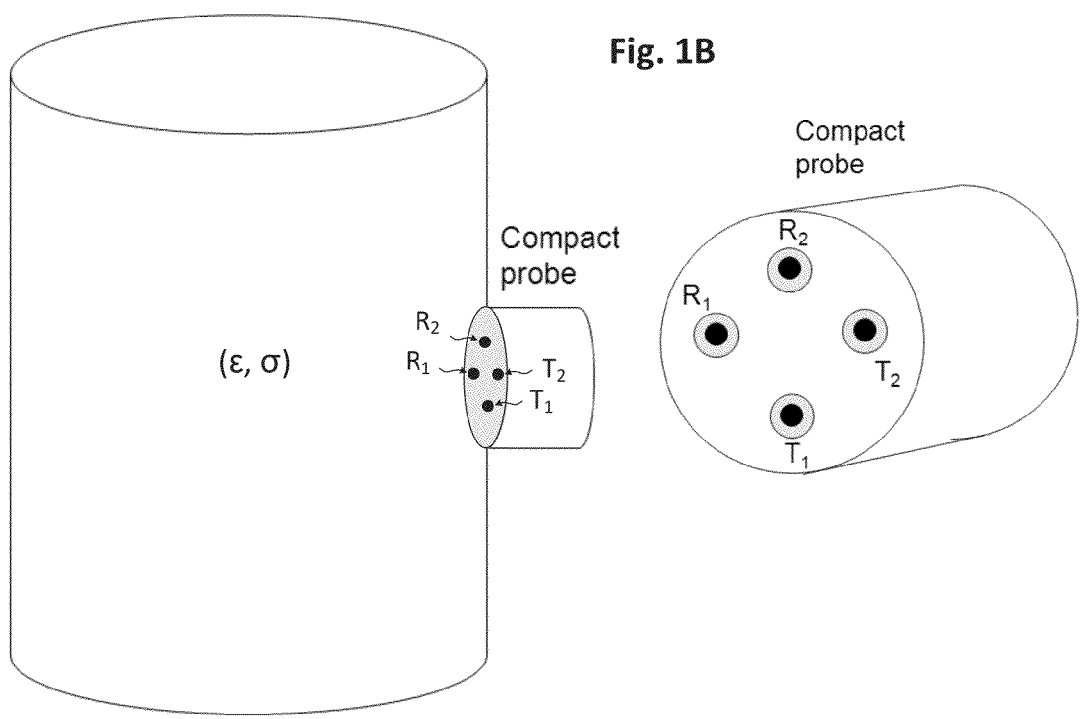
FIG. 1B is a schematic view of a conduit flush mounted with a compact probe comprising two open-ended-coaxial transmitters and two open-ended-coaxial receivers arranged to carry out the method of the present invention.

Turning to the drawing figures, as can be seen in FIG. 1A or FIG. 1B, four signals can be obtained from the different T-R combinations: near and far receiver measurements ($T_1R_1$) and ($T_1R_2$) from the transmitter $T_1$, and near and far receiver measurements ($T_2R_2$) and ($T_2R_1$) from the transmitter $T_2$. It can be appreciated that the measurement region of the compact probe shown in FIG. 1B is mainly in the vicinity of the 4-antenna aperture. These signals depend on the combined antenna element and electronic element gain ($G_T$, $G_R$) of the transmitting and receiving paths (e.g., a function of the transmitter-receiver electric/magnetic dipole areas and their load impedances, gains of transmitting and receiving amplifiers), and on the influence of the multiphase flow medium that may be expressed with a function $f$ depending on antennas operating in a pure electric dipole mode or in a pure magnetic dipole mode, or both. This function $f$ depends on the wave number k of the flow mixture and the distance r between the transmitting-receiving antennas, and can be written as (see e.g., EP 1983357 of the Applicant):

$$f(k, r) \propto \begin{cases} \dfrac{e^{ikr}}{2\pi r^3}(1 - ikr) & \text{magnetic} - \text{dipole} \\ \dfrac{e^{ikr}}{4\pi r^3}(1 - ikr - k^2 r^2) & \text{electric} - \text{dipole} \end{cases} \quad (1)$$

Here the wave number k is defined as $$k = \frac{\omega}{c} \sqrt{\varepsilon + i \frac{\sigma}{\omega \varepsilon_o}}, \quad (2)$$

where $\varepsilon$ and $\sigma$ are the flow mixture relative permittivity (dielectric constant) and conductivity, respectively; c is the speed of light in vacuum, $\omega$ the angular frequency of transmission RF/microwave, and $\varepsilon_0$=8.854 pF/m.

With respect to FIG. 1A, with a two-transmitter two-receiver configuration (with $r_1$ and $r_2$ being the distances between transmitters and receivers), the following four transmission absolute-measurement signals (being complex of magnitude and phase), obtainable from each of the four combinations of transmitter and receiving antenna, can be written as:

$$\begin{cases} V_{T_1,R_1} = G_{T_1} G_{R_1} f(k, r_1), & V_{T_1,R_2} = G_{T_1} G_{R_2} f(k, r_2) \\ V_{T_2,R_1} = G_{T_2} G_{R_1} f(k, r_2), & V_{T_2,R_2} = G_{T_2} G_{R_2} f(k, r_1) \end{cases} \quad (3)$$

It can be seen from equation 3 that, the effect of the (short- and long-term) variations in the overall gains ($G_{T1}$, $G_{T2}$, $G_{R1}$, $G_{R2}$) of both the transmitting antennas ($T_1$, $T_2$) and the receiving antennas ($R_1$, $R_2$) influence the signal reading between any one transmitting antenna and any one receiving antenna.

It is possible to process the ratio of the absolute complex measurement of two of the receivers with respect to a single (common) transmitter ($T_1$ or $T_2$). These signals can be combined and related to the measured attenuation A and phase-shift $\phi$, as follows:

$$A_{T_1} - i\phi_{T_1} = \ln\left(\frac{V_{T_1,R_1}}{V_{T_1,R_2}}\right) \quad (4a)$$
$$= \ln\left(\frac{G_{T_1} G_{R_1} f(k, r_1)}{G_{T_1} G_{R_2} f(k, r_2)}\right)$$
$$= \ln\left(\frac{G_{R_1} f(k, r_1)}{G_{R_2} f(k, r_2)}\right)$$

$$A_{T_2} - i\phi_{T_2} = \ln\left(\frac{V_{T_2,R_2}}{V_{T_2,R_1}}\right) \quad (4b)$$
$$= \ln\left(\frac{G_{T_2} G_{R_2} f(k, r_1)}{G_{T_2} G_{R_1} f(k, r_2)}\right)$$
$$= \ln\left(\frac{G_{R_2} f(k, r_1)}{G_{R_1} f(k, r_2)}\right)$$

However, it can be seen from equation 4a or 4b that, the effect of the (short- and long-term) variations in the overall gains ($G_{R1}$, $G_{R2}$) of the receiving antennas ($R_1$, $R_2$) is not removed based on this differential measurement scheme involving combining the signals from one transmitter antenna with two receiving antennas. Note that the antenna spacings ($r_1$, $r_2$) have to be sufficiently different to make possible the determination of the flow mixture wave number $k(\in,\sigma)$ (of equation 2) from the measured attenuation A and/or phase-shift $\phi$.

However, for a scheme comprising the configuration shown in FIG. 1A or in FIG. 1B with two transmitting antennas ($T_1$, $T_2$) and two receiving antennas ($R_1$, $R_2$), and with two known but unequal spacings ($r_1$, $r_2$), the compensation method according to the present invention can then be applied. The compensation method enables eliminating further the effects of the gains of the receiving antennas that may be slightly different. The compensation method effectively involves the averaging of the two differential measurements given in equations 4a and 4b, viz.

$$A_{T_1,T_2} - i\phi_{T_1,T_2} = \frac{(A_{T_1} - i\phi_{T_1}) + (A_{T_2} - i\phi_{T_2})}{2} \qquad (5)$$

$$= \frac{1}{2}\left[\ln\left(\frac{G_{R_1}f(k,r_1)}{G_{R_2}f(k,r_2)}\right) + \ln\left(\frac{G_{R_2}f(k,r_1)}{G_{R_1}f(k,r_2)}\right)\right]$$

$$= \ln\left(\frac{f(k,r_1)}{f(k,r_2)}\right)$$

Thus, by processing the resulting attenuation $A_{T_1,T_2}$ and phase-shift $\phi_{T_1,T_2}$ derived from the signals at the receiving antennas relatively to the two transmitting antennas, operated e.g. according to antennas having pure magnetic dipole mode (see EP 1901094) or having pure electric dipole mode, or having both mode (see EP 1983357), it is possible to determine the electromagnetic properties (k) of the flow medium by means of a mathematical inversion algorithm.

For example, for the electric and magnetic dipole modes given in equation 1, the theoretical values of the compensated attenuation $A_{T_1,T_2}$ and phase-shift $\phi_{T_1,T_2}$ can be derived as follows:

$$A_{T_1,T_2} - i\phi_{T_1,T_2} = \qquad (6)$$

$$\begin{cases} 3\ln\left(\frac{r_1}{r_2}\right) + ik(r_2 - r_1) + \ln\left(\frac{1 - ikr_1 - k^2r_1^2}{1 - ikr_2 - k^2r_2^2}\right) & \text{electric-dipole} \\ 3\ln\left(\frac{r_1}{r_2}\right) + ik(r_2 - r_1) + \ln\left(\frac{1 - ikr_1}{1 - ikr_2}\right) & \text{magnetic-dipole} \end{cases}$$

Hence, given the transmitter-receiver spacings ($r_1$, $r_2$), from Equation 6, we can have in general the following two set of equations:

$$A_{T_1,T_2} = F_1(k) = F_1(\in,\sigma;\omega)$$

$$\phi_{T_1,T_2} = F_2(k) = F_2(\in,\sigma;\omega) \qquad (7)$$

The compensated measurement according to the present invention based on a magnetic dipole mode enables a deep radial depth of investigation into the flow mixture (e.g. into the gas-core in the case of an annular gas-liquid flow). The compensated measurement according to the invention based on an electric dipole mode enables a shallow radial depth of investigation into the flow mixture (e.g. near the liquid annular layer on the pipe wall in the case of an annular gas-liquid flow).

The compensated attenuation and phase-shift measurements ($A_{T_1,T_2}$, $\phi_{T_1,T_2}$) at one or a plurality of frequencies ($\omega$) are free from short- and long-term drift effects of the sensing antennas and their electronic circuits. Based on these compensated measurements, the permittivity $\in$ and the conductivity $\sigma$ of a multiphase flow (e.g., the entire gas-liquid mixture and/or the liquid annulus in the case of an annular flow) can be calculated by means of appropriate inversion calculations, from the set of inverse equations of the Equation 7. The water fraction of the flow mixture (e.g., the water-in-liquid-ratio WLR of the liquid annulus in the case of an annular flow) and the gas fraction of the flow mixture (e.g., the gas-core diameter in the case of an annular flow) can then be derived from the calculated permittivity $\in$ and the conductivity $\sigma$ of the flow, by the use of appropriate permittivity and conductivity mixing laws. The water conductivity $\sigma_{water}$ (salinity) can also be determined from the measured the mixture permittivity $\in$ and the mixture conductivity $\sigma$ for a multiphase mixture containing water (see U.S. Pat. No. 6,831,470). This facilitates a water fraction (and WLR) determination in a changing water salinity situation, for example due to formation water breakthrough or water flooding. A robust detection of the water fraction and water-salinity change is also important for subsea-well flow assurance, for the controlled injection of hydrate and/or corrosion inhibitors. Online water-salinity estimate from RF/microwave sensor also enables correction for the mass attenuation coefficients of the water calibration points of a dual-energy or multi-energy nuclear based multiphase flow meter (see U.S. Pat. No. 6,831,470).

Figure 2:
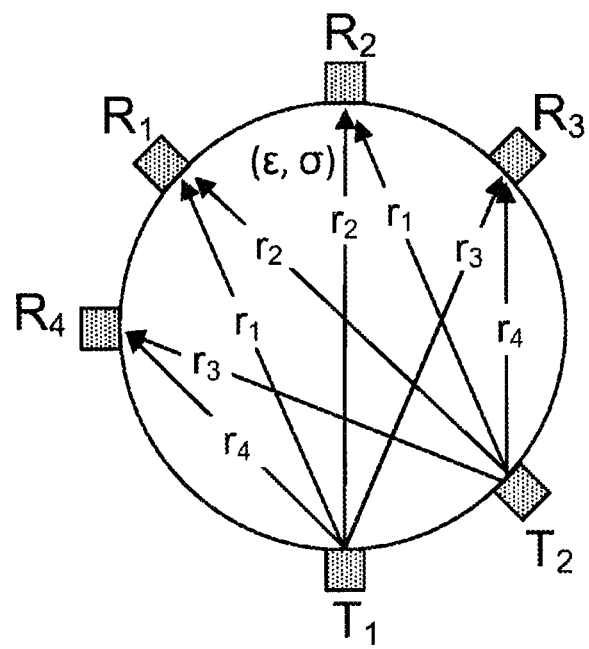
FIG. 2 is a schematic representation of a cross-sectional view through another conduit comprising two transmitters and four receivers arranged to carry out the method of the present invention.

FIG. 2 shows in cross-section, an arrangement of two transmitters, $T_1$ and $T_2$, and four receivers, $R_1$ to $R_4$. It is to be noted that there is a notional line of symmetry passing through the centre of the conduit. In this arrangement the method according to the invention described in relation to FIG. 1A can be carried out in two separate ways. Firstly, the method can be carried out involving transmitters $T_1$ and $T_2$ and receivers $R_1$ and $R_2$. Secondly, it can be carried out involving transmitters $T_1$ and $T_2$ and receivers $R_3$ and $R_4$. This will yield two compensated measurements of phase-shift and amplitude attenuation.

Figure 3:
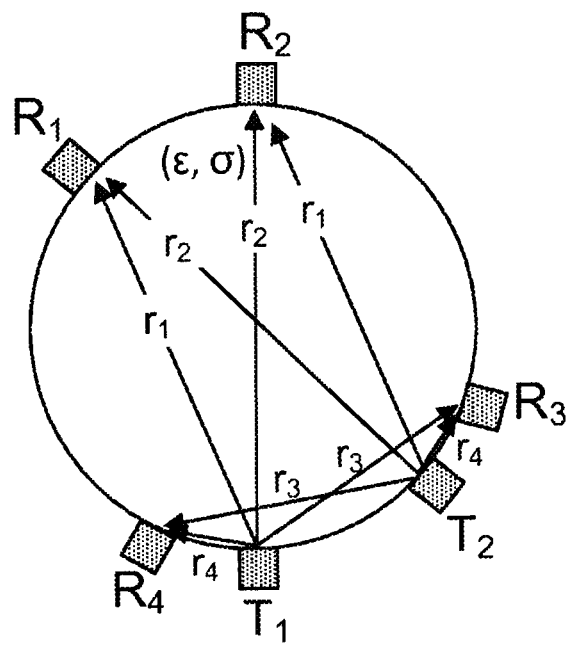
FIG. 3 is a schematic representation of a cross-sectional view of another conduit comprising two transmitters and four receivers arranged to carry out the method of the present invention.

FIG. 3 shows in cross-section, another arrangement of two transmitters $T_1$ and $T_2$ and four receivers $R_1$ to $R_4$. It is again to be noted the notional line of symmetry passing through the centre of the conduit. As for the arrangement shown in FIG. 2, this arrangement can establish two compensated measurements of phase-shift and amplitude attenuation. However, in view of the positioning of $R_3$ and $R_4$, the compensated measurement involving these receivers is sensitive to the fluid properties in the vicinity of the inner wall of the conduit. As the compensated measurement involving $R_1$ and $R_2$ provides flow information cross-pipe, this combination of the compensated measurements can be particularly informative, particularly if there is likely to be an annulus of liquid flowing along the inner wall of the conduit with a gas core in the centre, or if there is a stratified liquid layer at the underside of a horizontal conduit where receivers $R_3$ and $R_4$ (and transmitters $T_1$ and $T_2$) are co-located. Performing compensated measurements at the liquid water-rich region at a pipe underside, such as at the horizontal blind-tee inlet of a multiphase-flowmeter measurement pipe section, provides a more robust detection of water conductivity/salinity at multiphase and/or wet-gas (high gas-volume-fraction) flow conditions. It can be appreciated that a compact probe such as that shown in FIG. 1B can be used to perform compensated measurement of the properties of liquid (such as WLR, water salinity) in the vicinity of the compact-probe aperture that is preferably installed in a chosen liquid-rich region of a conduit (such as at the horizontal blind-tee inlet of a multiphase-flowmeter measurement pipe section).

Figure 4:
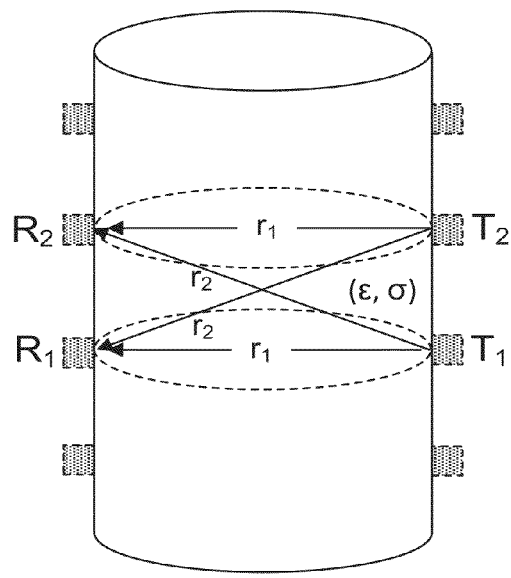
FIG. 4 is a schematic representation in oblique view of another conduit comprising two transmitters and two receivers arranged to carry out the method of the present invention.

FIG. 4 shows, in oblique view, another arrangement of two transmitters $T_1$ and $T_2$ and two receivers $R_1$ and $R_2$. In this arrangement the transmitters and receivers are not all located at the same axial position. However, it is to be noted that there is a line of symmetry passing through the centre of the conduit. The method of the invention as described in relation to the arrangement shown in FIG. 1A can be carried out in the same manner. This arrangement provides information extending along a portion of the length of the conduit, so may provide additional useful information.

Figure 5:
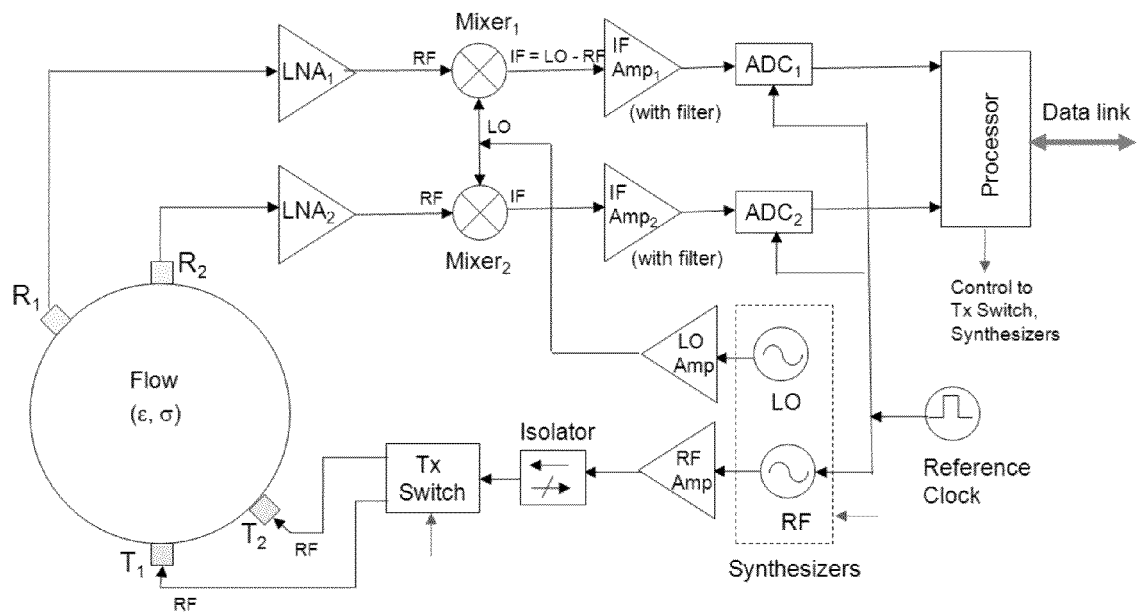
FIG. 5 is a circuit schematic diagram showing how two transmitters and two receivers can be employed according to the method of the invention.

FIG. 5 shows an exemplary schematic circuit diagram for the basic arrangement shown in FIG. 1A or FIG. 4, or in FIG. 1B in the case of a compact probe. A radio frequency (RF) synthesizer provides output energy in the microwave or radio frequency region of the spectrum (e.g., from 10 MHz to 10 GHz). A local oscillator frequency (LO) synthesizer is chosen to yield an Intermediate Frequency (IF=LO−RF) which is sufficiently high (e.g., >100 kHz) to enable rapid amplitude-phase measurement of all T-R combinations. The output of the RF synthesizer is coupled through an isolator to an electronic switch (Tx Switch), the two outputs of which connect to the transmitting antennas $T_1$ and $T_2$. The switch is controlled by a control signal from a processor energising each transmitter in turn, e.g., for a few microseconds each.

The receiving antennas $R_1$ and $R_2$ simultaneously detect the RF signal passing through the conduit which pass to a respective low-noise amplifier ($LNA_1$ and $LNA_2$). The amplified RF signals then pass to a respective mixer which is also fed with an appropriately amplified local oscillator (LO) signal. The down-converted $R_1$ and $R_2$ receivers' IF signals are then amplified once more with appropriate low-pass filtering and pass to analogue-to-digital converters for digitization before passing to the processor. The method of the invention can be carried out by suitable comparison of the transmitted and received signals. The amplitude-ratio and phase-difference are calculated by the processor, which also controls the sequencing of the Tx Switch to alternate the two transmitters (and the selection of RF and LO frequencies, amplifiers' gains etc.). The processor computes compensated transmission attenuation and phase measurements as of equation 5, at a desirable, rapid data rate and/or with proper time averaging, and performs subsequent flow-mixture permittivity and/or conductivity inversions and multiphase-flow phase fraction and/or water conductivity determinations. The processed data can be transmitted through a Data Link for recording/storage/display or further processing with combination of other measurements such as venturi differential-pressure and/or nuclear mixture density.

Figure 6:
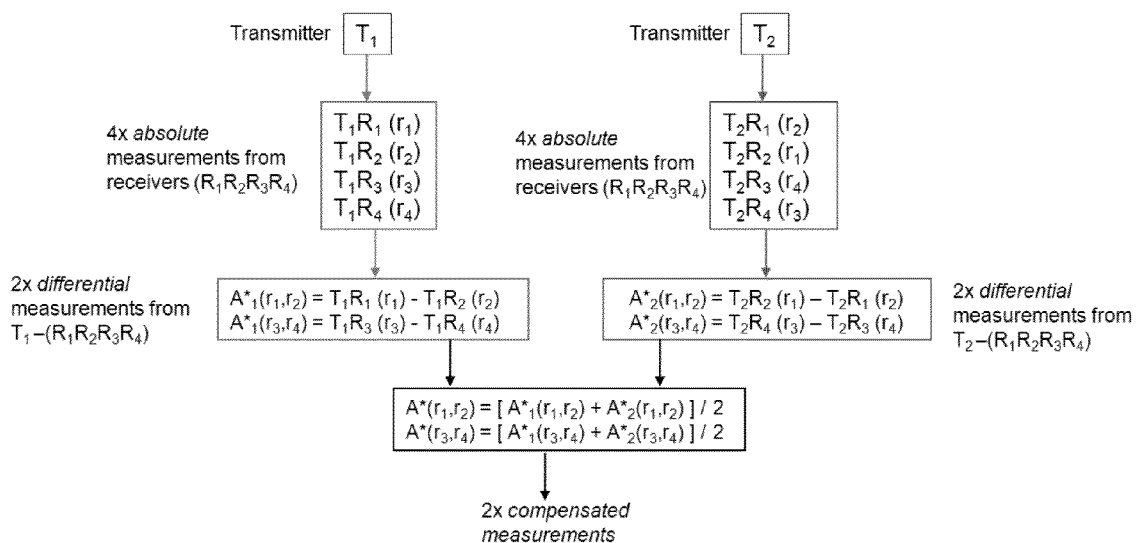
FIG. 6 is a flow chart, illustrating how the signals from an arrangement having two transmitters and four receivers can be combined according to the method of the present invention.

FIG. 6 is a flow diagram, illustrating how the signals from an arrangement comprising two transmitters, $T_1$ and $T_2$, and four receivers, $R_1$ to $R_4$, such as that shown in FIG. 2 or FIG. 3, can be combined to produce two compensated measurements according to the invention.

Figure 7:
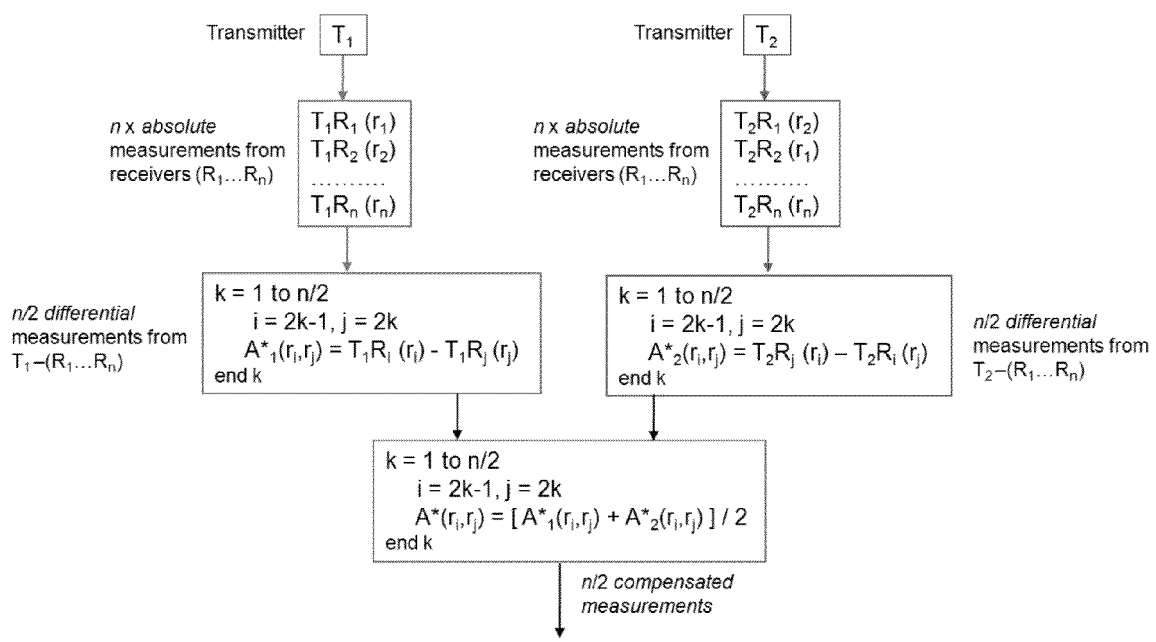
FIG. 7 is a flow chart, illustrating how the signals from a general arrangement having two transmitters and n receivers can be combined according to the method of the present invention.

FIG. 7 is a flow diagram, illustrating how the signals from an arrangement comprising two transmitters, $T_1$ and $T_2$, and n receivers, where n is an even number, can be combined to produce n/2 compensated measurements according to the invention.

The underlying method of compensated measurements of this invention should be applicable to other low-frequency electrical measurement techniques, such as those based on electrical capacitance, electrical resistance or conductance, electrical impedance and/or electrical inductance methods, or based on their combinations. This includes electrical tomography methods involving the use of multiple capacitance, resistance, impedance sensing electrodes, or inductance sensing coils, for performing compensated measurements of various appropriate electrode-pair or coil-pair combinations, in a same pipe cross section or in different pipe cross sections.

The underlying method of compensated measurements of this invention should be applicable to other higher frequency electrical measurement techniques, such as those based on millimeter-wave (or Terahertz frequency) measurement techniques, including Terahertz tomography-based methods.

Those skilled in the art would appreciate that the underlying method of compensated RF/microwave measurements of this invention for robust mixture permittivity and/or conductivity measurements can be used in combination with a gamma-ray or X-ray densitometer, and in combination with a multi-energy gamma-ray or multi-energy X-ray system.

Further, any of the above can be used in combination with a differential-pressure device. The differential-pressure device is preferably a venturi tube or a venturi nozzle.

The invention claimed is:

1. A method of measuring the permittivity and/or conductivity of a multiphase fluid flowing through a conduit, the method comprising
    measuring the signal from a first electromagnetic transmitter to a first electromagnetic receiver separated by a first distance across the conduit,
    measuring the signal from the first electromagnetic transmitter to a second electromagnetic receiver separated by a second distance across the conduit,
    measuring the signal from a second electromagnetic transmitter to the first electromagnetic receiver separated by a distance substantially equal to the second distance across the conduit,
    measuring the signal from the second electromagnetic transmitter to the second electromagnetic receiver separated by a distance substantially equal to the first distance across the conduit,
    wherein the first and second distances are substantially different and wherein any variation in gain values applied to the transmitters and receivers affects the measurements of signals;
    using a ratio of the signals received by the first and second receivers from the first transmitter to derive a first measurement of phase shift and amplitude attenuation;
    using a ratio of the signals received by the first and second receivers from the second transmitter to derive a second measurement of phase shift and amplitude attenuation; and
    avoiding dependence on gain values by averaging the first and second measurements of phase shift and amplitude attenuation to obtain a measurement of the phase-shift and amplitude attenuation which is independent of the gain values applied to the receivers and transmitters and thereby provide an estimate of the permittivity and/or conductivity of the multiphase fluid.

2. A method according to claim 1, wherein a transmitting and receiving antenna is able to operate as a pure magnetic dipole and/or as a pure electric dipole.

3. A method according to claim 2, wherein the transmitting and receiving antennas are able to operate as both pure magnetic and pure electric dipoles.

4. A method according to claim 1, wherein the signals are transmitted at one or more frequencies in the range of from 10 MHz to 10 GHz.

5. A method according to claim 1, wherein the difference between the first and the second distance is at least 10%, more preferably at least 20%.

6. A method according to claim 1, wherein "substantially equal" means that the respective distances are within 1% of the first and second distance respectively, preferably within 0.5%.

7. A method according to claim 1, wherein the conduit has a circular cross-section.

8. A method according to claim 1, wherein the first distance spans substantially diametrically across the conduit and the second distance spans substantially adjacent an inside wall of the conduit.

9. A method according to claim 1, carried out in a surface topside, subsea wellhead or downhole environment.

10. A method according to claim 1, wherein the transmitters and receivers are flush mounted in the wall of the conduit.

* * * * *